(12) United States Patent
Hutchins

(10) Patent No.: US 8,796,326 B1
(45) Date of Patent: Aug. 5, 2014

(54) FIRE ANT KILLER (F.A.K.)/ INSECTICIDE

(76) Inventor: Harold V. Hutchins, Ninety Six, SC (US)

( * ) Notice: Subject to any disclaimer, the term of this patent is extended or adjusted under 35 U.S.C. 154(b) by 0 days.

(21) Appl. No.: 13/343,325

(22) Filed: Jan. 4, 2012

Related U.S. Application Data

(63) Continuation-in-part of application No. 12/471,373, filed on May 23, 2009, now Pat. No. 8,110,563.

(60) Provisional application No. 61/055,639, filed on May 23, 2008.

(51) Int. Cl.
*A61K 31/40* (2006.01)
*A01N 43/08* (2006.01)
*A61K 31/12* (2006.01)
*A61K 31/075* (2006.01)
*A01N 31/14* (2006.01)

(52) U.S. Cl.
USPC ........... 514/421; 514/461; 514/675; 514/690; 514/691; 514/715; 514/717; 514/718; 514/719; 514/720; 514/721

(58) Field of Classification Search
CPC ....... A01N 31/04; A01N 31/08; A01N 31/14; A01N 37/06; A01N 37/09; A01N 37/10
See application file for complete search history.

(56) References Cited

U.S. PATENT DOCUMENTS

| | | | |
|---|---|---|---|
| 3,575,349 A | 4/1971 | Stahl et al. | |
| 3,782,026 A | 1/1974 | Bridges et al. | |
| 4,160,336 A | 7/1979 | Query et al. | |
| 4,756,118 A | 7/1988 | Evans, II | |
| 4,768,306 A | 9/1988 | Hillbun | |
| 4,815,234 A | 3/1989 | Connolly | |
| 4,817,329 A | 4/1989 | Forbes | |
| 4,829,706 A | 5/1989 | Perry | |
| 4,891,222 A * | 1/1990 | Eichhoefer | 424/770 |
| 5,031,355 A | 7/1991 | Ryan | |
| 5,054,231 A | 10/1991 | Witherspoon | |
| 5,109,629 A | 5/1992 | King, Jr. et al. | |
| 5,154,018 A | 10/1992 | Livingston | |
| 5,198,467 A | 3/1993 | Milks | |
| 5,319,878 A | 6/1994 | Moffett et al. | |
| 5,325,626 A | 7/1994 | Jackson | |
| 5,501,032 A | 3/1996 | Pitman | |
| 5,561,942 A | 10/1996 | Mugno et al. | |
| 5,616,318 A * | 4/1997 | Dudney | 424/93.1 |
| 5,679,365 A | 10/1997 | Henderson et al. | |
| 5,700,039 A | 12/1997 | Manning | |
| 5,870,852 A | 2/1999 | Stanley | |
| 5,881,493 A | 3/1999 | Restive | |
| 5,946,851 A | 9/1999 | Adey et al. | |
| 6,026,609 A | 2/2000 | Rawls | |
| 6,079,149 A | 6/2000 | Hastings | |
| 6,308,454 B1 | 10/2001 | Powell | |
| 6,604,318 B1 | 8/2003 | Cassidy | |
| 6,609,330 B1 | 8/2003 | Heitman | |
| 6,797,490 B2 | 9/2004 | Bulla, Jr. et al. | |
| 6,908,052 B1 | 6/2005 | Jacobson | |
| 6,966,143 B2 | 11/2005 | Allen | |
| 7,363,746 B2 | 4/2008 | Spies et al. | |
| 8,110,563 B1 * | 2/2012 | Hutchins | 514/150 |
| 2003/0131523 A1 | 7/2003 | Rawls | |
| 2005/0155278 A1 | 7/2005 | Rawls | |
| 2006/0073180 A1 | 4/2006 | Steward | |
| 2007/0056209 A1 | 3/2007 | Schuster | |
| 2007/0137095 A1 | 6/2007 | Chen | |
| 2008/0070787 A1 * | 3/2008 | Pullen | 504/362 |
| 2009/0208546 A1 * | 8/2009 | Shirley et al. | 424/405 |
| 2011/0039907 A1 * | 2/2011 | Cosky et al. | 514/407 |

* cited by examiner

*Primary Examiner* — Alton Pryor

(57) ABSTRACT

A fire ant killer chemical composition (the "FAK Composition") for effective killing of fire ants where the FAK Composition utilizes a minimal amount of active ingredients thereby significantly reducing safety concerns with respect to the use of said active ingredients, the FAK composition having a dish detergent composition and an insecticide composition.

2 Claims, 6 Drawing Sheets

FIG. 1

| Spectrum Group<br>Division of United Industries<br>P. O. Box 142642<br>St. Louis, MO 63114-0642 | Hazardous Material Identification System – (HMIS) ||
|---|---|---|
| | HEALTH – 2 | REACTIVITY – 0 |
| Material Safety Data Sheet<br>Complies with OSHA's Hazard Communication Standard, 29 CFR 1910.1200 | FLAMMABILITY – 0 | PERSONAL – |

I Trade Name: Spectracide® Triazicide® Insect Killer Once & Done!™ Concentrate$_2$

Product Type: Liquid dilutable insecticide concentrate

| Product Item Number: HG-95829 | Formula Code Number: 21-1065 |||
|---|---|---|---|
| EPA Registration Number | Manufacturer | Emergency Telephone Numbers ||
| 9688-277-8845 | Chemsico<br>Division of United Industries Corporation<br>8494 Chapin Industrial Drive<br>St. Louis, MO 63114 | For Chemical Emergency:<br>For Information:<br>Prepared by:<br>Date Prepared: | 1-800-633-2873<br>1-800-917-5438<br>C. A. Duckworth<br>July 9, 2009 |

II Hazards Ingredient/Identity Information

| Chemical | % | OSHA PEL | ACGIH TLV |
|---|---|---|---|
| Gamma-cyhalothrin<br>CAS #76703-62-3 | 0.08 | NE | NE |

III Physical and Chemical Characteristics

| | |
|---|---|
| Appearance & Odor: | Water-thin, translucent, straw color liquid with a slight odor. |
| Boiling Point: | 220° F |
| Melting Point: | NA |
| Ph | 5.0-6.0 |
| Specific Gravity: | 1.0 ($H_2O$ = 1) |
| Vapor Density: | Greater than 1 (Air = 1) |
| % Volatile (by vol.): | 95% |
| Solubility in Water: | >99% |
| Evaporation Rate: | Less than 1 (Butyl Acetate = 1) |

IV Fire and Explosive Hazards Data

| | |
|---|---|
| Flash Point: | >200°F |
| Flammable Limits: | NA |
| Autoignition Temperature: | NA |
| Fire Extinguishing Media: | Water fog, Carbon dioxide, Dry chemical |
| Decomposition Temperature: | NA |
| Special Fire-Fighting Procedures: | Use procedures for elimination of original fire source. |
| Unusual Fire & Explosion Hazards: | None. Also see Section V. |

V Reactivity Data

| | |
|---|---|
| Stability: | Stable |
| Polymerization: | Will not occur |
| Conditions to Avoid: | None |
| Incompatible Materials: | NA |
| Hazardous Decomposition or Byproducts: | NA |

VI Health Hazard Data

Ingestion (Swallowing): Harmful if swallowed. *First Aid:* Call a Poison Control Center immediately for treatment advice. Have person sip a glass of water if able to swallow. Do not induce vomiting unless told to do so by a Poison Control Center or doctor. Do not give anything by mouth to an unconscious person.

Special Notes: Have the product label with you when calling a Poison Control Center or doctor.

Health conditions Aggravated by Exposure: None known

Ingredients listed by NTP, OSHA, or IARC as Carcinogens or Potential Carcinogens: None

VII Precautions for Safe Handling and Use

Steps to be Taken in Case Material is Released or Spilled:
Avoid contact with liquid. Soak up with absorbent material.

Waste Disposal:
Nonrefillable container. Do not reuse or refill container. Place empty container in trash or recycle if available. If partially empty call your local solid waste agency for disposal instructions. Never place unused product down and indoor or outdoor drain.

Handling & Storage Precautions:
Store in a cool, dry area away from heat or open flame.

VIII Control Measures

Read and follow label directions. They are your best guide to using this product effectively, and give necessary safety precautions to protect your health.

IX Transportation Data

DOT: Not Regulated by DOT (limited quantity exception)
IMDG: Not Regulated by IMDG (limited quantity exception)
IATA: Not Regulated by IATA (limited quantity exception)

The information and statements herein are believed to be reliable but are not to be construed as warranty or representation for which we assume legal responsibility. Users should undertake sufficient verification and testing to determine the suitability for their own particular purpose of any information or products referred to herein. NO WARRANTY OF FITNESS FOR A PARTICULAR PURPOSE IS MADE.

FIG. 2a

The Procter & Gamble Company
P&G Household Care
Fabric & Home Care Innovation Center
5299 Spring Grove Avenue
Cincinnati, OH 45217-1087

MATERIAL SAFETY DATA SHEET

MSDS #:     RQ1102048                         Issue Date: 12/20/2011
Supersedes: RQ1008529                         Issue Date: 01/04/2011

SECTION I - PRODUCT IDENTIFICATION

Identity: Liquid Hand Dishwashing Detergents and Antibacterial Hand Soaps        Finished Product
Brands: ULTRA DAWN Blue [95435353]
Lemon [98960813]

Orange Dishwashing Liquid/Antibacterial Hand Soap [99697890],
Apple Blossom Dishwashing Liquid/Antibacterial Hand Soap [99697885]
Extra Action Dishwashing Liquid/Antibacterial Hand Soap [99697880]

Pure Essentials Sparkling Mist [98822285]
Pure Essentials Citrus Infusion [98827120]

Honeysuckle & Rain [95064063]
Jasmine & Lavender [95361409]
Hawaiian Pineapple [99618407]
Thai Dragonfruit [99618406]
New Zealand Springs [99618408]
Mediteranean Lavender [99858577]

P&G Telephone Number: 1-800-725-3296
or call Local Poison Control Center or your physician.

SECTION II - HAZARDS IDENTIFICATION

Potential Health Hazards (Acute and Chronic): (See Section 11 for more information)
Ingestion: Ingestion may cause transient gastrointestinal irritation.
Eye Contact: May cause mild, transient irritation.
Skin: Transient irritation with prolonged exposure to concentrated material.
Inhalation: N/A
Signs and Symptoms of Exposure:
Ingestion: May result in nausea, vomiting, and/or diarrhea.
Eye Contact: May cause stinging, tearing, itching, swelling, and/or redness.
Skin: Prolonged contact with concentrated material may be drying or transiently irritating to skin.
Inhalation: N/A
Potential Environmental Effects: (See Section 12 for more information)

FIG. 2b

SECTION III - COMPOSITION AND INGREDIENTS

Ingredients listed on the product label are: biodegradable surfactants and no phosphate. For antibacterial hand soaps, active ingredient is triclosan at 0.1%. Inactive ingredients for antibacterial hand soaps are listed in the Drug Facts box on back label.

Hazardous Ingredients as defined by OSHA, 29 CFR 1910.1200, and/or WHMIS under the HPA:

| Chemical Name | Common Name | CAS No. | Composition Range | LD50/LC50 |
|---|---|---|---|---|
| Ethyl alcohol | Ethanol | 64-17-5 | 1-5% | LD50(oral, rat) – 7.06 g/kg |
| Alcohol Ethoxysulfate, sodium salt | Sodium Laureth Sulfate | 68585-34-2 | 10-30% total anionic surfactant | LD50 (oral, rat) - >2g/kg |
| Alcohol Sulfates, sodium salt | Sodium Lauryl Sulfate | 68585-47-7 | | LD50 (oral, rat) - >2g/kg |
| Amines, C10-16 alkyldimethyl, N-oxides | Alkyl Dimethyl Amine Oxide | 70592-80-2 | 3 - 7% | LD50 (oral, rat) - 1.33 g/kg |

These substances are listed because in their pure bulk form they meet the OSHA and/or WHMIS definition of hazardous. Any hazards associated with this finished product are listed in Section II of this MSDS.

SECTION IV - FIRST AID INFORMATION

First Aid Procedures:

Ingestion: Drink 1 or 2 glasses of water.

Eye Contact: Flush thoroughly with water for 15 minutes.

Skin: If prolonged contact occurs, rinse thoroughly with water. If spilled on clothing, change clothes. If symptoms persist or recur, seek medical attention.

Inhalation: N/A

Other: Consumer product package has the following precautionary statement on the back label: "For external use only. Keep out of the reach of children. If Dawn gets in eyes, rinse thoroughly with water. If swallowed, drink a glass of water to dilute."

SECTION V - FIRE FIGHTING INFORMATION

Flammable Properties: The liquid hand dishwashing detergents have a flashpoint of 115-135°F (46.1-57.2°C) Pensky-Martens (Closed cup). However, the detergents do not sustain combustion according to ASTM D4206.

Flammable Properties:
Upper Flammable Limit: N/A
Lower Flammable Limit: N/A

Explosive Limits: UEL: N/A    LEL: N/A

Auto-ignition Temperature: N/A

Hazardous Combustion Products: N/A

Explosion Data (Sensitivity to Mechanical Impact): N/A
Explosion Data (Sensitivity to Static Discharge): N/A

Extinguishing Media:
Suitable: $CO_2$, water or dry chemical may be used.
Unsuitable: N/K

Protection of Firefighters:
Specific Hazards Arising from the Material: None.

SECTION VI - ACCIDENTAL RELEASE MEASURES

Personal Precautions: None

Environmental Precautions: DISPOSAL IS TO BE PERFORMED IN COMPLIANCE WITH ALL FEDERAL, STATE AND LOCAL REGULATIONS. Solutions of the detergents may be allowed to be flushed down sewer - First check with your local water treatment plant. Recycling is recommended for undiluted scrap product. Do not landfill.

Steps To Be Taken in Case Material is Released or Spilled: Prevent spills from reaching a waterway. Sorbents may be used. Read "Waste Disposal Method" below for further information.

FIG. 2c

SECTION VII - HANDLING AND STORAGE
Precautions To Be Taken in Handling: No special precautions necessary.
Precautions To B e Taken in Storage: No special precautions necessary.

SECTION VIII - EXPOSURE CONTROLS / PERSONAL PROTECTION
Recommended Exposure Guidelines: Ethanol (CAS# 64-17-5) ACGIH-TLV 1000 ppm
OSHA Z-1 PEL 1000 ppm
Engineering Controls: N/A
Personal Protective Equipment (PPE): N/A
Eye/Face Protection: None required with normal household use.
*Industrial Setting*: For splash protection, use chemical goggles. Eye wash fountain is recommended.
Skin Protection: None required with normal household use.
*Industrial Setting:* Protective gloves (rubber, neoprene) should be used for prolonged direct contact.
Respiratory Protection: No special precautions for casual exposure.
Ventilation *Local Exhaust*: None required with normal consumer use. *Special*: None
*Industrial (General)*: Normal/general dilution ventilation is acceptable. *Other*: None

SECTION IX - PHYSICAL AND CHEMICAL PROPERTIES

| | |
|---|---|
| Appearance (color, physical form, shape): Clear, opaque or colored liquids. | Flash Point (Method Used): 115-135°F (46.1-57.2°C) Pensky-Martens (Closed cup) but do not sustain combustion according to ASTM D4206. |
| Odor: Perfumed | Reserve Alkalinity: N/A |
| Odor Threshold: N/A | Solubility in Water: Complete |
| Physical State: Liquid hand dishwashing solution | Decomposition Temperature: N/K |
| Vapor Pressure (mm Hg): N/K | Evaporation Rate (nBuOAc=1): N/K |
| Vapor Density (Air=1): N/K | Specific Gravity/Density: ca. 1 |
| Boiling Point: N/K | Melting/Freezing Point: ~30 °F (-1.1°C) |
| Partition Coefficient (n-octanol/water): N/K | pH (10% solution): 9 |

Volatile Organic Compound (VOC): Not applicable - Product not regulated for VOC Content at State or Federal level

SECTION X - STABILITY AND REACTIVITY
Chemical Stability: Stable
Conditions to Avoid: None known
Incompatible Materials: None
Hazardous Decomposition Products: None known
Possibility of Hazardous Reactions: None known

SECTION XI - TOXICOLOGICAL INFORMATION
Liquid hand dishwashing detergents have a relatively low order of toxicity, may cause transient irritation and are expected to be emetic.
Chronic Effects: No chronic health effects reported.
Target Organs: No target organs reported.
Carcinogenicity: This finished product is not carcinogenic. NTP: No   IARC: No   OSHA: No

SECTION XII - ECOLOGICAL INFORMATION
All surfactants are readily biodegradable.

Ultra Dawn Hand Dishwashing Liquids and Antibacterial Hand Soaps

| SECTION XIII – DISPOSAL CONSIDERATIONS |
|---|
| Waste Disposal Method: DISPOSAL SHOULD BE IN ACCORDANCE WITH FEDERAL, STATE/PROVINCIAL AND LOCAL REGULATIONS<br><br>*Non Household Setting*: Products covered by this MSDS, in their original form, when disposed as waste, are considered non hazardous waste according to Federal RCRA regulations (40 CFR 261). Disposal should be in accordance with local, state and federal regulations. Solutions of diluted detergent in the course of use, may be allowed to be flushed down sewer. First check with your local water treatment plant. Recycling is recommended for undiluted scrap product. Do not landfill.<br><br>California Hazardous Waste: Not hazardous, in accordance with 22 CCR 66261.20 through 22 CCR 66261.24<br><br>*Household Use:* Household product is safe for disposal down the drain during detergent use or in the trash. Dispose of empty bottle in the trash or recyle where facilities exist. |

| SECTION XIV – TRANSPORT INFORMATION |
|---|
| Products covered by this MSDS, in their original form, are not regulated for transportation. |
| Ground Transport (US DOT): Not regulated |
| Air Transport (IATA): Not regulated |
| Marine/Water Transport (IMDG): Not regulated |

| SECTION XV – REGULATORY INFORMATION |
|---|
| United States<br>All intentionally-added components of this product are listed on the US TSCA Inventory.<br>This product is not subject to warning labeling under California Proposition 65.<br>EPA Reg. No.: Not Applicable<br><br>This product contains the following SARA 313/302/304/311/312 chemicals:<br>None<br><br>This product contains the following CERCLA chemicals:<br>Chemical Name     CAS Number     Max Range in Product (%)<br>Ethanol             64-17-5            5.0%<br><br>State Right-to-Know:<br>The following ingredients present in the finished product are listed on state right-to-know lists or state worker exposure lists: |

| Ingredient | CAS # | Max Level | State | | | | |
|---|---|---|---|---|---|---|---|
|  |  |  | IL | MA | NJ | PA | RI |
| Ethanol | 64-17-5 | 5.0 % | X | X | X | X | X |

Perfumes contained within the products covered by this MSDS comply with appropriate IFRA guidance

Canada
All ingredients are CEPA approved for import to Canada by Procter & Gamble. This product has been classified in accordance with the hazard criteria of the Canadian Controlled Products Regulations (CPR) and this MSDS contains all information required by the Controlled Products Regulations.

FIG. 2e

| SECTION XVI - OTHER INFORMATION |
|---|
| Perfumes contained within the products covered by this MSDS comply with appropriate IFRA guidance. |
| P&G Hazard Rating: Health: 1     4=EXTREME<br>                        Flammability: 1     3=HIGH<br>                        Reactivity: 0     2=MODERATE<br>                                            1=SLIGHT<br>                                            0=NOT SIGNIFICANT<br>*N/A. - Not Applicable       *N/K. - Not Known |
| Data supplied is for use only in connection with occupational safety and health. |
| DISCLAIMER: This MSDS is intended to provide a brief summary of our knowledge and guidance regarding the use of this material. The information contained here has been compiled from sources considered by Procter & Gamble to be dependable and is accurate to the best of the Company's knowledge. It is not meant to be an all-inclusive document on worldwide hazard communication regulations.<br><br>This information is offered in good faith. Each user of this material needs to evaluate the conditions of use and design the appropriate protective mechanisms to prevent employee exposures, property damage or release to the environment. Procter & Gamble assumed no responsibility for injury to the recipient or third persons, or for any damage to any property resulting from misuse of the product. |

FIRE ANT KILLER (F.A.K.)/ INSECTICIDE

CROSS REFERENCE

The present non-provisional patent application is a continuation-in-part of U.S. patent application Ser. No. 12/471,373 filed May, 23, 2009, which claims benefit to provisional patent application Ser. No. 61/055,639, the disclosures of which are incorporated in its entirety herein by reference.

BACKGROUND OF THE INVENTION

FAK is a chemical composition created for the eradication of fire ants and their mound. FAK destroys on contact as opposed to the granular mixes which require time to activate. FAK is an environmentally friendly insecticide that can be used in multiple scenarios ranging from spot spraying the mounds in any location around a home or business to spraying inside the home or business. When properly prepared, FAK kills the first few fire ants and saturates deep into the colony or mound to kill the eggs and queen in minutes and is immediately safe for activities involving pets or children.

BRIEF DESCRIPTION OF THE DRAWINGS

FIG. 1 shows an MSDS sheet for one possible insecticide composition: Spectracide's Triazicide Insect Killer Once and Done! Concentrate.

FIGS. 2a to 2e shows the Material Safety Data Sheets (MSDS) for one possible dish detergent composition: Ultra Dawn Apple Blossom Dishwashing liquid.

DESCRIPTION OF PREFERRED EMBODIMENTS

The present invention features a composition (the "FAK Composition") for killing fire ants. In some embodiments, the FAK Composition comprises an insecticide composition and a dish detergent composition. In some embodiments, the FAK Composition is a liquid composition.

In some embodiments, the insecticide contained within the insecticide composition comprises a pyrethroid insecticide, the active agent for the insecticide composition. Two brand names for products available in the public market that can be used as insecticide compositions for the present invention and which are products that contain a pyrethroid are Spectracide's "Triazicide", and "Hot Shot". Both products are manufactured by Spectrum Group, a division of United industries Corporation and can be purchased online or at a variety of retails stores such as Loews, Home Depot, or Wal-Mart. Spectracide's "Triazicide Insect Killer Once & Done Concentrate" ("Once and Done"), for example, a possible insecticide composition, is manufactured by Spectrum Group and Spectrum Group is located at P.O. Box 142642, St. Louis, Mo. 63114-0642. Once and Done has a product number of HG-95829 and a formula code of 21-1065.

Spectracide's Triazicide and Hot Shot products contain a pyrethroid insecticide where the concentration of the pyrethroid ranges from 0.002% to 0.08%, depending on the given specific product type. For example, as reflected in FIG. 1, the Triazicide product, Once and Done contains a pyrethroid, Gamma-Cyhalothrin at 0.08%.

The dish detergent composition can comprise a dish detergent available on the open market such as dish detergents by Dawn, Joy, Palmolive and Equate dish detergents. It is believed that the active agent in the dish detergent composition is a chlorinated phenol microbial agent. For example, Dawn Apple Blossom Dishwashing Liquid/Antibacterial Hand Soap, a possible dish detergent composition for the present invention, can be obtained via Dawn's parent company, The Procter & Gamble Company, located at 5299 Spring Grove Avenue in Cincinnati, Ohio, 45217-1087. Dawn's Apple Blossom Dishwashing liquid contains a chlorinated phenol microbial agent, triclosan, at 0.01% (See FIG. 2).

In some embodiments, the dish detergent composition comprises less than 0.1% of a chlorinated phenol microbial agent. One example of a chlorinated phenol microbial agent is triclosan (IUPAC name is 5-chloro-2-(2,4-dichlorophenoxy)phenol)), and is found in soaps and detergent at about 0.001-1.00%. Triclosan is also found in deodorants, toothpastes, shaving creams, mouth washes, and cleaning supplies and is infused in an increasing number of consumer products, such as kitchen utensils, toys, bedding, socks, and trash bags. Triclosan has been shown to be effective in reducing and controlling bacterial contamination on the hands and on treated products. More recently, showering or bathing with 2% triclosan has become a recommended regimen for the decolonization of patients whose skin is carrying methicillin resistant *Staphylococcus aureus* (MRSA) following the successful control of MRSA outbreaks in several clinical settings. Triclosan is regulated by the U.S. Food and Drug Administration, the Environmental Protection Agency, and the European Union. Detergent products known to have triclosan include Dawn, Joy, Palmolive and Equate dish detergents.

Table 1 shows the ingredients for a variety of publicly available dish detergent products which can comprise the dish detergent composition for the present invention.

TABLE 1

| Detergent | Ingredients |
| --- | --- |
| Ultra Dawn Anti-Bacterial | Water, sodium lauryl sulfate, sodium laureth sulfate, alkyl dimethyl amine oxide, SD alcohol, sodium chloride, PPG-26, PEI-14 PEG-10/PPG-7 copolymer, cyclohexanediamine, magnesium chloride, phenoxyethanol, triclosan, methylisothiazolinone, fragrance, D & C Red 33, FD & C Yellow 5 |
| Joy Anti-Bacterial | Water, sodium lauryl sulfate, sodium laureth sulfate, alkyl dimethyl amine oxide, sodium chloride, PPG-26, PEI-14 PEG-10/PPG-7 copolymer, cyclohexanediamine, phenoxyethanol, triclosan, methylisothiazolinone, fragrance, D & C Red 33, FD & C Yellow 5 |
| Palmolive Ultra Antibacterial | Water, sodium laureth sulfate, lauramidopropyl betaine, sodium dodecylbenzene sulfonate, SD 3A alcohol, lactic Acid, sodium xylene sulfonate, fragrance, tetrasodium EDTA, dyes |

In some embodiments, the dish detergent composition further comprises one or more of the following ingredients: sodium lauryl sulfate, sodium laureth sulfate, C12-14.16 dimethyl amine oxide, SD alcohol, sodium chloride, PPG-26, PEI-14 PEG-10/PPG-7 copolymer, cyclohexanediamine, phenoxyethanol, magnesium chloride, methylisothlazolinone, fragrance, D &C Red 33, FD&C Yellow 5.

In some embodiments, the dish detergent composition comprises one or more of the following ingredients: sodium lauryl sulfate, sodium laureth sulfate, C12-14.16 dimethyl amine oxide, SD alcohol, sodium chloride, PPG-26, PEI-14 PEG-10/PPG-7 copolymer, cyclohexanediamine, phenoxyethanol, magnesium chloride, methylisothlazolinone, fragrance, D &C Red 33, FD&C Yellow 5.

It is believe that the present invention is not anticipated or obvious in light of prior art and that the present invention is extremely advantageous because it uses only a fraction of the insecticides and antimicrobial agents active in the insecticide compositions and dish detergent compositions, respectively. As such, the present invention is much safer for use and is much different from the prior art because of the extremely low levels of active ingredients present in the FAK Composition. The FAK Composition comprises the dish detergent composition comprising a chlorinated phenol; and the insecticide composition comprising a pyrethroid. In the FAK Composition the percentage of the dish detergent composition ranges from 0.0001% to 5% of the FAK Composition and the percentage of the insecticide composition ranges from 0.0001% to 5% of the FAK Composition and wherein the chlorinated phenol is present in an amount ranging from $1.0 \times 10^{-10}\%$ to 0.01% in the FAK Composition and wherein the percentage of the pyrethroid is present in an amount ranging from $1.0 \times 10^{-20}\%$ to 0.08% in the FAK Composition.

Furthermore, for use, the FAK Composition above may be diluted. For example, the FAK Composition may be diluted at about 1-3 ounces, e.g., 2 ounces, to about 0.75 to 1.25, e.g., about 1 gallon or 128 fl ounces, of a solution (meaning that the percentage of the combination of the dish detergent composition and the insecticide compositions, the active ingredients of the FAK Composition, can be reduced to just 0.015 of the overall diluted FAK Composition. In some embodiments, the solution comprises water. In some embodiments, the FAK Composition is diluted with water at a ratio of 2 ounces of FAK Composition to 1 gallon of water.

The following protocols are non-limiting examples for preparation and use of the FAK Composition.

EXAMPLES

Using a 2:1 Mixture of Dish Detergent Composition to Insecticide Composition INITIAL MIXTURE (Concentrated form): In some embodiments, a FAK composition can be formulated as follows. First combine two gallons (256 fl. ounces) of dish detergent composition with one gallon (128 fl. ounces) of insecticide composition to form an initial mixture.

Next, isolate 2 fluid ounces of the initial mixture.

DILUTION: Dilute the 2 fluid ounces of the Initial Mixture by combining the 2 fluid ounces of the initial mixture with 128 fl. ounces of an inactive solution to arrive at the final FAK Composition. This example final FAK Composition results in a composition wherein the active ingredients, the Insecticide composition and the dish detergent composition, make up just 1.5% of the final FAK composition.

This example embodiment results in a FAK Composition comprising approximately 1.0% of a dish detergent composition and approximately 0.5% of an insecticide composition.

It is important to illustrate that both the formation of the initial mixture and the dilution steps significantly reduce the concentration of the active agents contained within the FAK Composition. These changes can be displayed mathematically as follows, where it is assumed that no chemical reactions affect said changes and where it is assumed merely for example purposes that the initial concentrations of the active agents in both the insecticide composition and the dish detergent composition, prior to combination of the initial mixture and dilution, are 0.01%.

Percentage Change in Active Agents after Initial Mixture (Concentrated)
→ Determine new percentages of Agents $$P_{DDC}^F = V1(P_{DDC})/(V1+V2)$$

$$P_{IC}^F = V2(P_{IC})/(V1+V2)$$

Where $P_{DDC}$=Starting Percentage of DDC active agent, $P_{IC}$=Starting Percentage of IC active agent, V1=Volume of DDC, and V2=Volume of IC
and
$P_{DDC}^F$=New percentage of DDC active agent after combining with IC
and
$P_{IC}^F$=New percentage of IC active agent after combining with DDC Solving for $P1^F$ and $P2^F$ using the preferred embodiment:

$$P_{DDC}^F=(256(0.01))/(256+128)=2.56/384$$

$$P_{DDC}^F=0.0066\%$$

$$P_{IC}^F=(128(0.01))/(256+128)=1.28/384$$

$$P_{IC}^F=0.0033\%$$

Thus, as the above calculations illustrate, the preferred embodiment results in an initial mixture where the concentration of the active agents in the insecticide composition and dish detergent composition is reduced proportionally corresponding to the ratio of dish detergent composition to insecticide composition combined in the Initial Mixture. The initial mixture is also referred to herein as the concentrate or concentrated form of a FAK Composition. In order to formulate the final FAK Composition, the FAK Composition concentrate can be diluted.

During Dilution, the concentration of the active agents is reduced further, as illustrated below.

Percentage Change in Active Agents (POST Dilution)

Dilution: Combine 2 fluid ounces of the above FAK initial mixture (concentrate) with 128 fl ounces of inactive ingredient solution such as water:

$$PD_{DDC}=2(0.0066)/(2+128)=0.0132/130$$

$$PD_{DDC}=1.015^{-4}\%$$

$$PD_{IC}=2(0.0033)/(2+128)=0.0066/130$$

$$PD_{IC}=5.07^{-5}\%$$

Where $PD_{DDC}$=Percentage of DDC active agent in a diluted version of the above embodiment and $PD_{IC}$=percentage of IC active agent in a diluted version of the above embodiment.

As the above calculations demonstrate, the final FAK Composition contains concentrations of active agents that are mere fractions of the initial concentrations found in the insecticide and dish detergent compositions.

The above example is not limiting of the present invention and one skilled in the art would recognize that the above possible embodiment is just one possible iteration for combining an insecticide composition and a dish detergent composition to formulate a FAK Composition. For example, the ratio of dish detergent composition to insecticide composition could be 3:1 or, as another example, the ratio of dish detergent composition to insecticide composition could be 1:2 resulting in a higher concentration of insecticide composition in the FAK composition. The following table illustrates such possible embodiments.

TABLE 2

| Diluted FAK - 2 oz. concentrate FAK: 128 oz. water | % of Insecticide Composition in FAK Composition | % of Dish Detergent Composition in FAK Composition |
|---|---|---|
| Composition 1 | .513% | 1.03% |
| Composition 2 diluted | .384% | 1.15% |

TABLE 2-continued

| Diluted FAK - 2 oz. concentrate FAK: 128 oz. water | % of Insecticide Composition in FAK Composition | % of Dish Detergent Composition in FAK Composition |
|---|---|---|
| Composition 3 diluted | .3%-.2% | 1.2%-1.3% |
| Composition 4 diluted | .1%-05% | 1.4%-1.45 |
| Composition 5 diluted | .513-1.0% | 1.03%-.05% |
| Composition 6 diluted | 1.0%-1.4% | .05%-.01% |

In addition, as recognized earlier, the concentrations of the active ingredients contained within insecticide compositions and dish detergent compositions may vary according to the product used for each composition. The following table illustrates the possible embodiments both for concentrated or pre-dilution FAK Compositions and FAK Compositions post dilution.

TABLE 3

| Concentrated FAK - 1 part insecticide: 2 part dish detergent | Pyrethroid | Chlorinated Phenol |
|---|---|---|
| Composition 1 | .026% | .0066% |
| Composition 2 | .001%-.1% | .00001%-.01% |
| Composition 3 | .0001%-1.0% | .000001%-.1% |
| Composition 4 | .000001%-10% | .0000001%-1.0% |
| Composition 5 | .0000001%-15% | .00000001%-10% |

TABLE 4

| Diluted FAK - 2 oz. concentrate FAK: 128 oz. water | Pyrethroid | Chlorinated Phenol |
|---|---|---|
| Composition 1 diluted | .0004% | $1.015^{-4}$% |
| Composition 2 diluted | .00001%-.001% | .00001%-.001% |
| Composition 3 diluted | .000001%-.01% | .000001%-.01% |
| Composition 4 diluted | .0000001%-.1% | .0000001%-.1% |

Example for Preparing a Diluted FAK Composition and Suggested Use

Preparation of diluted FAK composition for use: Measure 2 ounces of FAK Composition concentrate per gallon of water. Pour FAK Composition into sprayer already with desired amount of water in sprayer. Agitate mound without spreading ants or dirt. Immediately spray the diluted FAK composition onto the agitated mound to totally saturate the mound and 1-2 feet area around the base of the mound.

The FAK composition may be used in the following ways:

(A) Perimeter spray as other insecticide is used to provide barrier protection and residue kill.

(B) Broadcast spray over large areas such as yards, animal pens, fields, gardens, and trees.

(C) Applied directly on pets as a spray or shampoo for fleas.

(D) Mixed with ornamental grass herbicides for dual application.

(E) FAK can also kill other ants, spiders, roaches, wasps, beetles and fleas. It has also been used to kill the spinning worms on pecan trees without harming other wildlife.

Non-Market Product FAK Composition Embodiment

In addition to the above embodiments, one skilled in the art would recognize that a FAK Composition could be developed by isolating only the specific active agents contained within the insecticide composition and the dish detergent composition and combining the same. As such, a FAK Composition could be developed by combining only an insecticide agent (pyrethroid), and an anti-microbial agent (chlorinated phenol), without including all of the additional ingredients contained within ordinary market products that happen to contain an insecticide agent or anti-microbial agent, such as Dawn for an anti-microbial agent, or Hot Shot for an insecticide agent.

In addition, it would be appreciate by one skilled in the art that a non-market product FAK Composition containing only the insecticide agent and the anti-microbial agent could further comprise additional ingredients to increase the efficacy of such a FAK Composition.

As used herein, the term "about" refers to plus or minus 10% of the referenced number.

The disclosures of the following U.S. Patents are incorporated in their entirety by reference herein: U.S. Pat. No. 20080070787, U.S. Pat. No. 20090208546.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the above possible embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

In addition to ants, the present invention can effectively be applied to other insects such as Chiggers, White Grub, Japanese Beetle, Crickets, Fleas, Ticks (dog and deer), mites, Carpenter Ants, Red Ants, and Household Ants, cockroaches, palmetto bug, aphids (all-fruit/flowering), cutworms, caterpillar, June beetle, cutworm, stink bug, grasshopper, maggots, fly, fruit worm, wasp, hornets, yellow jackets, cicada, fruit tree borer, and all types of spiders. The present invention can be sprayed inside and outside of a house, building or structure.

What is claimed is:

1. A fire ant killer chemical composition (the "FAK Composition") effective in killing of fire ants where the FAK Composition utilizes a minimal amount of active ingredients thereby significantly reducing safety concerns with respect to the use of said active ingredients, the FAK composition comprising:

a) a dish detergent composition wherein the dish detergent composition comprises a chlorinated phenol; and
   b) an insecticide composition wherein the insecticide composition comprises a pyrethroid
   wherein the percentage in the dish detergent composition is present in an amount ranging from 0.0001% to 5% of the FAK Composition and wherein the percentage of the insecticide composition is present in an amount ranging from 0.0001% to 5% in the FAK Composition and wherein the chlorinated is present in an amount ranging from $1.0 \times 10^{-10}$% to 0.01% in the FAK Composition and wherein the percentage of the pyrethroid is present in an amount ranging from $1.0 \times 10^{-20}$% to 0.08% in the FAK Composition.

2. A method of killing fire ant eggs deposited or embedded within an ant hill, the method comprising spraying the composition of claim 1 into the fire ant hill or mound.

* * * * *